US011065414B2

(12) United States Patent
Coleman et al.

(10) Patent No.: US 11,065,414 B2
(45) Date of Patent: *Jul. 20, 2021

(54) COMPONENT FOR MEDICAL CIRCUIT

(71) Applicant: FISHER & PAYKEL HEALTHCARE LIMITED, Auckland (NZ)

(72) Inventors: Peter Nigel Coleman, Auckland (NZ); Nathan Lee Gray, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 331 days.

This patent is subject to a terminal disclaimer.

(21) Appl. No.: 16/056,176

(22) Filed: Aug. 6, 2018

(65) Prior Publication Data
US 2019/0070382 A1 Mar. 7, 2019

Related U.S. Application Data

(63) Continuation of application No. 14/115,806, filed as application No. PCT/NZ2012/000059 on May 2, 2012, now Pat. No. 10,213,571.

(Continued)

(51) Int. Cl.
*A61M 16/08* (2006.01)
*A61M 16/10* (2006.01)
(Continued)

(52) U.S. Cl.
CPC .... *A61M 16/1095* (2014.02); *A61M 16/0003* (2014.02); *A61M 16/0057* (2013.01);
(Continued)

(58) Field of Classification Search
CPC .......... A61M 16/0003; A61M 16/0057; A61M 16/06; A61M 16/0841; A61M 16/0875;
(Continued)

(56) References Cited

U.S. PATENT DOCUMENTS 3,163,707 A 12/1964 Darling
3,636,285 A 1/1972 Wickham et al.
(Continued)

FOREIGN PATENT DOCUMENTS

CN 1341463 A 3/2002
CN 1846802 A 10/2006
(Continued)

OTHER PUBLICATIONS

International Search Report; Application No. PCT/NZ2012/000059; Filed May 2, 2012.
(Continued)

*Primary Examiner* — Annette Dixon
(74) *Attorney, Agent, or Firm* — Knobbe, Martens, Olson & Bear, LLP

(57) ABSTRACT

A medical tube has a tube wall defining a passageway for transportation of gases and further has a first end and a second end. At least one end of the medical tube comprises one or more of a pre-formed pneumatic port component, a pre-formed electrical port component, and a pre-formed sensor port component. A cuff is over-moulded about and thereby connects the pneumatic port component, the electrical port component, and/or the sensor port component and at least a portion of the tube end.

23 Claims, 5 Drawing Sheets

Related U.S. Application Data

(60) Provisional application No. 61/483,215, filed on May 6, 2011, provisional application No. 61/596,798, filed on Feb. 9, 2012.

(51) Int. Cl.
*A61M 16/00* (2006.01)
*A61M 16/06* (2006.01)
*A61M 16/16* (2006.01)

(52) U.S. Cl.
CPC ........ *A61M 16/06* (2013.01); *A61M 16/0841* (2014.02); *A61M 16/0875* (2013.01); *A61M 16/0883* (2014.02); *A61M 16/16* (2013.01)

(58) Field of Classification Search
CPC .......... A61M 16/0883; A61M 16/1095; A61M 16/16
See application file for complete search history.

(56) References Cited

U.S. PATENT DOCUMENTS

| | | | |
|---|---|---|---|
| 3,733,697 A | 5/1973 | Wickham et al. | |
| 4,967,744 A | 11/1990 | Chua | |
| 6,126,610 A | 10/2000 | Rich et al. | |
| 6,571,794 B1 | 6/2003 | Hansen | |
| 6,953,354 B2 | 10/2005 | Edirisuriya et al. | |
| 7,096,864 B1 | 8/2006 | Mayer et al. | |
| 7,469,719 B2 | 12/2008 | Gray | |
| 8,210,173 B2 | 7/2012 | Vandine | |
| 8,726,901 B2 | 5/2014 | Jassell et al. | |
| 8,733,349 B2 | 5/2014 | Bath et al. | |
| 10,213,571 B2 * | 2/2019 | Coleman | A61M 16/0057 |
| 2003/0207601 A1 | 11/2003 | Adachi | |
| 2008/0105257 A1 | 5/2008 | Klasek et al. | |
| 2008/0251073 A1 | 10/2008 | Jassell et al. | |
| 2010/0280454 A1 | 11/2010 | Rosiello | |
| 2011/0023874 A1 | 2/2011 | Bath et al. | |
| 2011/0108031 A1 | 5/2011 | Korneff et al. | |
| 2017/0197055 A1 * | 7/2017 | Moody | A61M 16/1095 |

FOREIGN PATENT DOCUMENTS

| | | |
|---|---|---|
| CN | 1964756 A | 5/2007 |
| CN | 101537221 | 9/2009 |
| CN | 101541367 A | 9/2009 |
| CN | 101579551 A | 11/2009 |
| CN | 101808689 A | 8/2010 |
| EP | 2098260 A1 | 9/2009 |
| WO | WO 2007/051230 A1 | 5/2007 |
| WO | WO 2008/055307 A1 | 5/2008 |
| WO | WO 2009/022004 A2 | 5/2012 |

OTHER PUBLICATIONS

English Translation of Search Report of TW Patent Application No. 101116016, dated Jun. 8, 2016, 4 pages.
Chinese Patent Office, Office Action, Application No. CN 109111778, dated Jan. 26, 2021, in 19 pages.

* cited by examiner

COMPONENT FOR MEDICAL CIRCUIT

INCORPORATION BY REFERENCE TO ANY PRIORITY APPLICATIONS

Any and all application for which a foreign or domestic priority claim is identified in the Application Data Sheet as filed with the present application are hereby incorporated by reference in their entireties and made a part of the present disclosure.

BACKGROUND OF THE INVENTION

Field of the Invention

The present invention relates to components for medical circuits. In one particular aspect, the invention relates to breathing tubes for use in the inspiratory and/or expiratory limb of a breathing circuit, including heated breathing tubes. In another aspect the invention relates to a tube component for a surgical insufflation system, including a heated insufflator tubes.

Description of the Related Art

In medical applications, such as with assisted breathing, the gases inhaled by a patient preferably are delivered in a condition having humidity near saturation level and at close to body temperature (e.g., usually at a temperature between 33° C. and 37° C.). In facilitating delivery of gases to a patient in such preferred conditions, breathing tubes (or medical tubes) may be used that include heaters. However, some systems may not necessarily require heaters.

Condensation or rain-out can form on the inside surfaces of the breathing tubes as the high humidity breathing gases cool and/or come into contact with the relatively cooler breathing tube surface. Breathing gases exhaled by a patient are usually returned fully saturated and flow through an expiratory breathing tube. If the expired gas is allowed to cool as it passes along an expiratory breathing tube, condensation or rain-out may also occur.

Similarly, Continuous Positive Airway Pressure (CPAP) systems or positive pressure ventilation systems that provide patients suffering from obstructive sleep apnoea (OSA) with positive pressure breathing gases also use breathing tubes for delivering (or removing) inspiratory (and/or expiratory) gases.

Condensate forming in a breathing tube (either inspiratory or expiratory) can be breathed or inhaled by a patient and may lead to coughing fits or other discomfort. Condensation within a breathing tube may also interfere with the performance of connected equipment and ancillary devices and/or various sensors.

Attempts have been made to reduce the adverse effects of condensation by either reducing the level of condensation or providing collection points for draining condensed liquid from the tubing component. Reducing the condensation or rain-out has generally been attempted by maintaining or elevating the temperature above the dew point temperature of the breathing gas to reduce the formation of condensation. This temperature is typically maintained by a heater wire within the breathing tube, although the rain-out performance of these breathing tubes may not be complete due to a number of factors. Further, previous methods of heating the gases flow to reduce rain-out, typically result in heated tubing that has been expensive and/or difficult to manufacture. Particularly, in 'single use' applications such as typically found in hospital applications, the manufacturing cost of breathing tubes is important. It is highly desirable to even further reduce rainout, while preferably maintaining a low production cost, for example, by utilising a manufacturing method that is capable of high production speeds.

Similarly, during laparoscopic surgery with insufflation, it may also be desirable for the insufflation gas (commonly $CO_2$) to be humidified before being passed into the abdominal cavity. This can help prevent 'drying out' of the patient's internal organs, and can decrease the amount of time needed for recovery from surgery. Even when dry insufflation gas is employed, the gas can become saturated as it picks up moisture from the patient's body cavity. The moisture in the gases tends to condense out onto the walls of the medical tubing or discharge limb of the insufflation system. The water vapour can also condense on other components of the insufflation system, such as filters for example. Any vapour condensing on the filter and run-off along the limbs (inlet or exhaust) from moisture is highly undesirable. For example, water that has condensed on the walls can saturate the filter and cause it to become blocked. The blockage potentially causes an increase in back pressure and hinders the ability of the system to clear smoke. Further, liquid water in the limbs can run into other connected equipment, which is undesirable.

However, despite systems utilised for minimising condensation or rain-out, many such breathing tubes or conduit are provided as single use products. That is, they are used for a specified (limited) period of time or with a single (or individual) patient or person receiving care. Such single use is recommended for hygiene and sterility purposes. That may be because, generally, such tubes are provided in an un-used condition and with a high initial level of sterility. Once such tubes are used for the specified (e.g., limited) period of time, or the treatment or care of an individual patient or person receiving care has ended, the tube is disposed. However, not all markets are able to afford the cost associated with single use products. It would, therefore, be advantageous to be able to provide an alternative conduit for such medical circuits to be of a configuration enabling reuse. There are economic and practical considerations associated with reusable conduits.

In respect of reusable conduits for breathing applications, it would be advantageous to provide associated conduit components that are capable of reuse or that go at least some way towards enabling a reuse capability of the conduit.

In this specification, where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description, which is given by way of example only.

SUMMARY OF THE INVENTION

It is an object of the present invention to provide a conduit and/or method of manufacturing a conduit that will at least go some way towards improving on the above or which will at least provide the public or the medical profession with a useful choice.

According to a first aspect of the invention, there is provided a medical tube comprising:

a tube wall defining a passageway for transportation of gas, and having a first end and a second end (such as, for example, a machine end and a patient end), the passageway providing for fluid communication between the ends, wherein at least one end of the medical tube comprises:

a cuff over-moulded about and attaching of one or more first pre-formed component(s), one or more second pre-formed component(s), and at least a portion of the at least one tube end, such that in use, the first pre-formed component or components is in fluid communication with the passageway, the, or each, first pre-formed component configured for fluid connection with a further component(s) of a breathing circuit, and the second pre-formed component or components is receivable of an auxiliary medical tube appliance.

Preferably the first pre-formed component comprises a pneumatic port, the pneumatic port providing for pneumatic connection with the at least one end of the passageway Preferably the pneumatic port is substantially axially aligned with the passageway.

Preferably the pneumatic port is substantially aligned with the passageway such that pneumatic connection between the port and the passageway is provided.

Preferably the pneumatic port is a tubular body having a longitudinal axis, such as a substantially cylindrical housing.

Preferably the at least one second pre-formed component is attachable to at least a part or parts of the at least one tube end.

Preferably the second pre-formed component comprises one or more locators extending from the component for attachment to at least a part or parts of the tube end.

Preferably the locator(s) is attachable to a section or sections of a wall forming the passageway or the at least one end of the tube.

Preferably the locator(s) is/are a clip or clips.

Preferably the at least one second pre-formed component comprises a port, the port receivable of the auxiliary appliance.

Preferably the auxiliary appliance is a sensor for sensing one or more characteristics of gas in the passageway.

Preferably the at least one second pre-formed component comprises a sensor port, the sensor port receivable of a sensor for sensing one or more characteristics of gas in the passageway.

Preferably the sensor port is arranged such that a sensor located by the sensor port is positioned to be in fluid communication with the passageway and substantially perpendicular to flow of gas in the passageway.

Preferably the sensor receivable by the port senses one or more of gas temperature, relative humidity, gas velocity (or flow rate) of gas in the passageway.

Preferably the sensor senses relative humidity.

Preferably where the second pre-formed component comprises a sensor port, the sensor is fluidly connected to or in fluid connection with the passageway.

Preferably the auxiliary appliance is an electrical supply for an electrically powered heater or heaters associated with the passageway of the tube.

Preferably the at least one second pre-formed component comprises an electrical port, the electrical port receivable of electrical connector for providing an electrical supply to one or more electrically powered heater or heaters associated with the passageway.

Preferably where the second pre-formed component comprises an electrical port, the electrical port is fluidly sealed from communication with the passageway.

Preferably the second pre-formed component is a body comprising at least one locator for attachment to at least a section of a wall forming the passageway or the at least one end of the tube.

Preferably the at least one locator comprises electrical connector(s) for electrically coupling the electrical connector with the one or more electrically powered heater or heaters associated with the passageway.

Preferably the electrical port is configured for providing an electrical connection to the heater or heaters.

Preferably the heater or heaters is/are located substantially within the passageway, or substantially within a wall of the passageway, or substantially about an exterior surface of the passageway.

Preferably the heater or heaters is/are located substantially about an exterior surface of the passageway.

Preferably the heater or heaters is/are a heater source for gas passing through the passageway.

Preferably the heater or heaters is/are one or more heater wires.

Preferably the over-moulded cuff forms a pneumatic seal about the at least one tube end and between the first pre-formed component(s) and the second pre-formed component(s), whilst maintaining fluid connection between the first pre-formed component(s) and the at least one end of the tube and passageway therein.

Preferably the cuff is formed from, or by, a single over-moulding procedure.

Preferably the cuff is directly attached during an over-moulding operation to an exterior surface of the at least one end of the tube.

Preferably the cuff is directly attached to the first pre-formed component(s) and the second pre-formed component(s) during the over-moulding operation.

Preferably there is no intermediate layer or protective collar or material is positioned between the over-moulded cuff and an exterior wall of the passageway, such as for preventing direct contact between the over-moulded cuff and the exterior wall of the passageway.

Preferably the cuff is formed by a single-step over-moulding operation.

Preferably the cuff is formed of a material having a lower relative melting point than that of the first and second pre-formed component(s), and material forming a wall of the passageway.

Preferably the cuff is formed of a material relatively more pliable than that of the first pre-formed component(s) and/or second pre-formed component(s).

Preferably the second pre-formed component is located longitudinally intermediate of the at least one end of the tube and the first pre-formed component.

Preferably the first pre-formed component is substantially axially aligned with the tube passageway, and/or the first pre-formed component is substantially aligned with the tube passageway such that pneumatic connection between the first pre-formed component and the passageway is provided.

Preferably the first pre-formed component comprises a sensor port and an electrical port as single pre-moulded component.

Preferably the interior of the passageway is of a smooth linear surface.

Preferably the interior of the passageway is devoid of corrugations, convolutions or undulations.

Preferably the tube wall is of a corrugated form.

Preferably the interior surface of the passageway is mechanically and/or chemically cleanable, and/or surfaces in contact with the gas is mechanically and/or chemically cleanable.

Preferably the tube is a reusable medical tube.

According to a second aspect of the invention, there is provided a medical tube comprising:

a tube wall defining a passageway for transportation of gas, and having a first end and a second end (such as, for example, a machine end and a patient end), the passageway providing for fluid communication between the ends, wherein at least one end of the medical tube comprises:

a pre-formed pneumatic port component in fluid communication with the passageway, the component configured for fluid connection with a further component(s) of a breathing circuit, a pre-formed sensor port component receivable of a sensor for sensing one or more characteristics of gas in the passageway, and a cuff over-moulded about and connecting of the pneumatic port component, sensor port component and at least a portion of the tube end.

Preferably the sensor port component is arranged such that a sensor located by the sensor port component is in fluid communication with the passageway and positioned to be substantially perpendicular to flow of gas in the passageway.

Preferably a sensor receivable by the sensor port component is sensing of one or more of gas temperature, relative humidity, gas velocity (or flow rate).

Preferably the sensor is fluidly connected to or in fluid connection with the passageway.

Preferably the pre-formed sensor port component comprises at least one locator for attachment to at least a section of a wall forming the passageway or the at least one end of the tube.

Preferably the at least one tube end further comprises a pre-formed electrical port component receivable of an electrical connection for providing an electrical circuit or pathway to one or more electrical appliances associated with the passageway, the cuff being additionally over-moulded of the pre-formed electrical port component.

Preferably the electrical appliance is at least one electrically powered heater associated with the passageway of the tube.

Preferably the heater is located substantially within the passageway, or substantially within a wall of the passageway, or substantially about an exterior surface of the passageway.

Preferably the heater is located substantially about an exterior surface of the passageway.

Preferably the heater is a heat source for gas passing through the passageway.

Preferably the heater is at least one heater wire.

Preferably the pre-formed electrical port component comprises at least one locator for attachment to at least a section of a wall forming the passageway or the at least one end of the tube.

Preferably the at least one locator comprises electrical connector(s) for electrically coupling the electrical connector with one or more electrically powered heater or heaters associated with the passageway.

Preferably the electrical port is fluidly sealed from communication with the passageway.

Preferably the pre-formed sensor port component and pre-formed electrical port component are a single pre-moulded component.

Preferably the over-moulded cuff forms a pneumatic seal about, at least, the at least one tube end and between the pre-formed pneumatic component and the pre-formed sensor port component, whilst maintaining fluid connection between the pre-formed pneumatic port component and the at least one end of the tube and passageway.

Preferably the cuff is directly attached during an over-moulding operation to, at least, an exterior surface of the at least one end of the tube, the pre-formed sensor port and the pre-formed pneumatic port.

Preferably the cuff is formed from, or by, a single over-moulding procedure.

Preferably there is no intermediate layer or protective collar or material is positioned between, at least, the over-moulded cuff and an exterior wall of the passageway, such as for preventing direct contact between the over-moulded cuff and the exterior wall of the passageway.

Preferably the cuff is formed of a material having a lower relative melting point than that of, at least, the pre-formed pneumatic port component, the pre-formed sensor port component, and material forming a wall of the passageway.

Preferably the cuff is formed of a material relatively more pliable than that of, at least, the pre-formed pneumatic port component and/or the pre-formed sensor port component.

Preferably the pre-formed sensor port component is located longitudinally intermediate of the at least one end and the pre-formed pneumatic port component.

Preferably the pre-formed pneumatic port component is substantially axially aligned with the tube passageway, and/or the pre-formed pneumatic port component is substantially aligned with the tube passageway such that pneumatic connection between the pre-formed pneumatic port component and the passageway is provided.

Preferably the interior of the passageway is of a smooth linear surface.

Preferably the interior of the passageway is devoid of corrugations, convolutions or undulations.

Preferably the wall is of a corrugated form.

Preferably the interior surface of the passageway is mechanically and/or chemically cleanable, and/or surfaces in contact with the gas is mechanically and/or chemically cleanable.

Preferably the tube is a reusable medical tube.

According to a third aspect of the invention, there is provided a medical tube comprising:

a tube wall defining a passageway for transportation of gas, and having a first end and a second end (such as, for example, a machine end and a patient end), the passageway providing for fluid communication between the ends, wherein at least one end of the medical tube comprises:

a pre-formed pneumatic port connector component in fluid communication with the passageway, the connector component configured for fluid connection with a further component(s) of a breathing circuit, a pre-formed electrical port component receivable of an electrical connection for providing an electrical circuit or pathway to one or more electrical appliances associated with the passageway, and a cuff over-moulded about and connecting of the pneumatic port component, electrical port component and at least a portion of the tube end.

Preferably the electrical appliance is at least one electrically powered heater associated with the passageway of the tube.

Preferably the heater is located substantially within the passageway, or substantially within a wall of the passageway, or substantially about an exterior surface of the passageway.

Preferably the heater is located substantially about an exterior surface of the passageway.

Preferably the heater is a heat source for gas passing through the passageway.

Preferably the heater is at least one heater wire.

Preferably the pre-formed electrical port component comprises at least one locator for attachment to at least a section of a wall forming the passageway or the at least one end of the tube.

Preferably the at least one locator comprises electrical connector(s) for electrically coupling the electrical connector with one or more electrically powered heater or heaters associated with the passageway.

Preferably the electrical port is fluidly sealed from communication with the passageway.

Preferably the at least one tube end further comprises a pre-formed sensor port component receivable of a sensor for sensing one or more characteristics of gas in the passageway, the cuff being additionally over-moulded of the pre-formed sensor port component.

Preferably the sensor port component is arranged such that a sensor located by the sensor port component is in fluid communication with the passageway and positioned to be substantially perpendicular to flow of gas in the passageway.

Preferably a sensor receivable by the sensor port component is sensing of one or more of gas temperature, relative humidity, gas velocity (or flow rate).

Preferably the sensor is fluidly connected to or in fluid connection with the passageway.

Preferably the pre-formed sensor port component comprises at least one locator for attachment to at least a section of a wall forming the passageway or the at least one end of the tube.

Preferably the sensor port and electrical port are a single pre-moulded component.

Preferably the over-moulded cuff forms a pneumatic seal about, at least, the at least one tube end and between the pre-formed electrical port component and the pre-formed pneumatic port component, whilst maintaining fluid connection between the pneumatic port and the at least one end of the tube and passageway.

Preferably the cuff is directly attached during an over-moulding operation to an exterior surface of the at least one end of the tube.

Preferably the cuff is directly attached to, at least, the pre-formed pneumatic port component, pre-formed electrical port component during an over-moulding procedure.

Preferably the cuff is formed from or by a single-step over-moulding procedure.

Preferably the pre-formed pneumatic port component provides for pneumatic connection with the at least one end of the passageway.

Preferably the pre-formed pneumatic port component is substantially axially aligned with the tube passageway and/or wherein the pre-formed pneumatic port component is substantially aligned with the tube passageway such that pneumatic connection between the pre-formed pneumatic port component and the passageway is provided.

Preferably the cuff is formed of a material having a lower relative melting point than that of, at least, the pneumatic port component, electrical port component, and passageway.

Preferably the cuff is formed of a material that is relatively more pliable that that of, at least, the pneumatic port component, electrical port component, and passageway.

Preferably the interior of the passageway is of a smooth linear surface.

Preferably the interior of the passageway is devoid of corrugations, convolutions or undulations.

Preferably the wall is of a corrugated form.

Preferably the interior surface of the passageway is mechanically and/or chemically cleanable, and/or surfaces in contact with the gas is mechanically and/or chemically cleanable.

Preferably the tube is a reusable medical tube.

According to a fourth aspect of the invention, there is provided a method for fabricating a medical tube comprising:

providing a length of tube, the length of tube comprising a tube wall defining a passageway for transportation of gas, and having a first end and a second end (such as, for example, a machine end and a patient end), the passageway providing for fluid communication between the ends, locating one or more first pre-formed component or components substantially adjacent to at least one of the ends of the tube, locating one or more second pre-formed component or components substantially at or to the at least one end of the tube, and in a single over-moulding procedure, over-moulding a cuff about the first pre-formed component(s) and second pre-formed component(s) and about at least a portion of the at least one end of the tube, the over-moulded cuff attaching to and locating the pre-moulded component(s) in place relative to the at least one end of the tube, such that in use, the first pre-formed component or components is in fluid communication with the passageway, the, or each, first pre-formed component configured for fluid connection with a further component(s) of a breathing circuit, and the second pre-formed appliance component or components is receivable of a tube appliance.

Preferably, in a moulding die, the at least one end of the tube is positioned in a tube receiving mould position, the first pre-formed component(s) is/are positioned in first pre-formed component receiving mould position, and the second pre-formed component(s) is/are positioned in a second pre-formed component receiving mould position, such that, the cuff is formed by over-moulding a moulding material about each of the pre-formed components and at least a portion of the at least one end of the tube.

Preferably, the first pre-formed component is a pneumatic port, the pneumatic port providing for pneumatic connection with the at least one end of the passageway.

More preferably, the pneumatic port aligning substantially axially with the tube passageway.

Alternatively preferably, the pneumatic port aligning substantially with the tube passageway such that pneumatic connection between the port and the passageway is provided.

Preferably, the pneumatic port is a tubular body having a longitudinal axis, such as a substantially cylindrical housing.

Preferably, the at least one second pre-formed appliance component is attachable to at least a part or parts of the at least one tube end.

More preferably, the second pre-formed component is attachable by one or more locators extending from the component.

Even more preferably, the locator(s) is/are a clip or clips.

Most preferably, the locator(s) is attachable to a section or sections of a wall forming the passageway and the at least one end of the tube.

Preferably, the second pre-formed component is a body comprising at least one locator for attachment to at least a section of a wall forming the passageway and the at least one end of the tube.

More preferably, the at least one locator comprises electrical connector(s) for electrically coupling an electrical appliance receivable by the second pre-formed component with one or more electrical appliances associated with the conduit or passageway.

Preferably, at least one second pre-formed appliance component comprises a sensor port, the sensor port receivable of a sensor for sensing one or more characteristics of gas in the passageway.

More preferably, the sensor port is arranged such that a sensor located by the sensor port is positioned to be substantially perpendicular to flow of gas in the passageway.

Even more preferably, a sensor receivable by the sensor port component is sensing of one or more of gas temperature, relative humidity, gas velocity (or flow rate).

Preferably, at least one second pre-formed appliance component is an electrical port receivable of an electrical appliance connection for providing an electrical circuit or pathway to one or more electrical appliances associated with the passageway.

More preferably, the electrical port is configured for providing an electrical connection to at least a heater wire.

Even more preferably, the heater wire is located substantially within the passageway, or substantially within a wall of the passageway, or substantially about an exterior surface of the passageway.

Yet even more preferably, the heater wire is located substantially about an exterior surface of the passageway.

Most preferably, the heater wire is a heater source for gas passing through the passageway.

Preferably, the electrical appliance associated with the passageway is electrically connected to or with the electrical port prior to the over-moulding.

Preferably, the heater wire is electrically connected to or with the electrical port prior to the over-moulding in the mould.

Preferably, the heater wire is soldered to electrical terminals of the electrical port.

Preferably, the interior of the passageway is of a smooth linear surface.

More preferably, the interior of the passageway is devoid of corrugations, convolutions or undulations.

Alternatively preferably, the interior of the passageway is capable of being mechanically and/or chemically cleaned.

Preferably, the over-moulded cuff forms a pneumatic seal about the at least one tube end and between the first pre-formed component(s) and the second pre-formed component(s), whilst maintaining fluid connection between the first pre-formed component(s) and the at least one end of the tube and passageway therein.

More preferably, the cuff is formed from, or by, a single over-moulding procedure.

Preferably, the cuff is directly attached during an over-moulding operation to an exterior surface of the at least one end of the tube.

Preferably, the cuff is directly attached to the first pre-formed component(s) and the second pre-formed component(s) during the over-moulding operation.

Preferably, the cuff is formed by a single-step over-moulding operation.

Preferably, the cuff is formed of a material having a lower melting point than that of the first and second pre-formed component(s), and material forming a wall of the passageway.

Preferably, the cuff is formed of a material more pliable than that of the first pre-formed component(s) and/or second pre-formed component(s).

Preferably, the second pre-formed component is located longitudinally intermediate of the at least one end and the first pre-formed component.

Alternatively preferably, the first pre-formed component comprises a sensor port and an electrical port as single pre-moulded component.

In respect of any one of the embodiments described above, such a second pre-formed component may provide for an electrical port and/or optionally a sensor port, wherein at least a portion of the component attaches to the tube by retention of a part of the tube end (e.g., a bead, rib, portion of a tube wall, or combinations of these) and the component.

Preferably, the component comprises a first part housing an electrical port and/or a sensor port and a second part configured to enclose a rear surface of the electrical port and/or sensor port part.

Preferably, the rear surface is provided for electrical connection between the electrical terminals of an electrical port and a heater wire(s) and/or sensor wire(s) or other electrical or sensor components carried by the tube.

Preferably, the first part or the second part (or both) comprises a channel or a recess or pathway or shaped channel region for heater wire(s) and/or sensor wire(s) extending carried by the tube extending from a tube part thereof to the rear surface for electrical connection to the electrical terminals.

Preferably, the one or more protrusions and one or more complimentary recesses are provided upon the first and second parts allowing such parts to fit together. More preferably, such a fit is a snap-fit or a friction-fit configuration.

Preferably, the first and second parts are provided with a folding region or a thinned region capable of folding or being folded, such that the first and second parts may be provided as a single part, and such parts may be fitted together.

Preferably, said component provides a housing or encasing for electrical connections between electrical terminals and electrical components carried by the tube. In some configurations, at least a part of the electrical port terminals provide for electrical connection to heater wire(s) (and/or sensor wire(s)) provided associated with the tube Preferably, the component provides for a secure retention between the component and at least a part or parts of the end of the tube. The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists not only in the foregoing but also envisages additional constructions of which the following gives examples only.

BRIEF DESCRIPTION OF THE DRAWINGS

Preferred embodiments of the invention will be described by way of example only and with reference to the drawings, in which.

DETAILED DESCRIPTION OF THE PREFERRED EMBODIMENT

In this specification, the terms "medical circuit" and "breathing circuit" are used to indicate the general field of the invention. It is to be understood that a "circuit" is intended to include open circuits, which do not form a complete closed circuit. For example, CPAP systems typically consist of a single inspiratory breathing tube between the blower and the patient interface. The term "breathing circuit" is intended to include such "open circuits." Similarly, the term "medical circuit" is intended to include both breathing circuits and insufflation circuits (which are also typically "open"). Similarly, the term "medical tubing" is intended to be read broadly and as flexible tubing suitable for use in the type of medical circuits described above connecting between components of a medical circuit and providing a low resistance gases pathway between components of a medical circuit.

Figure 1:
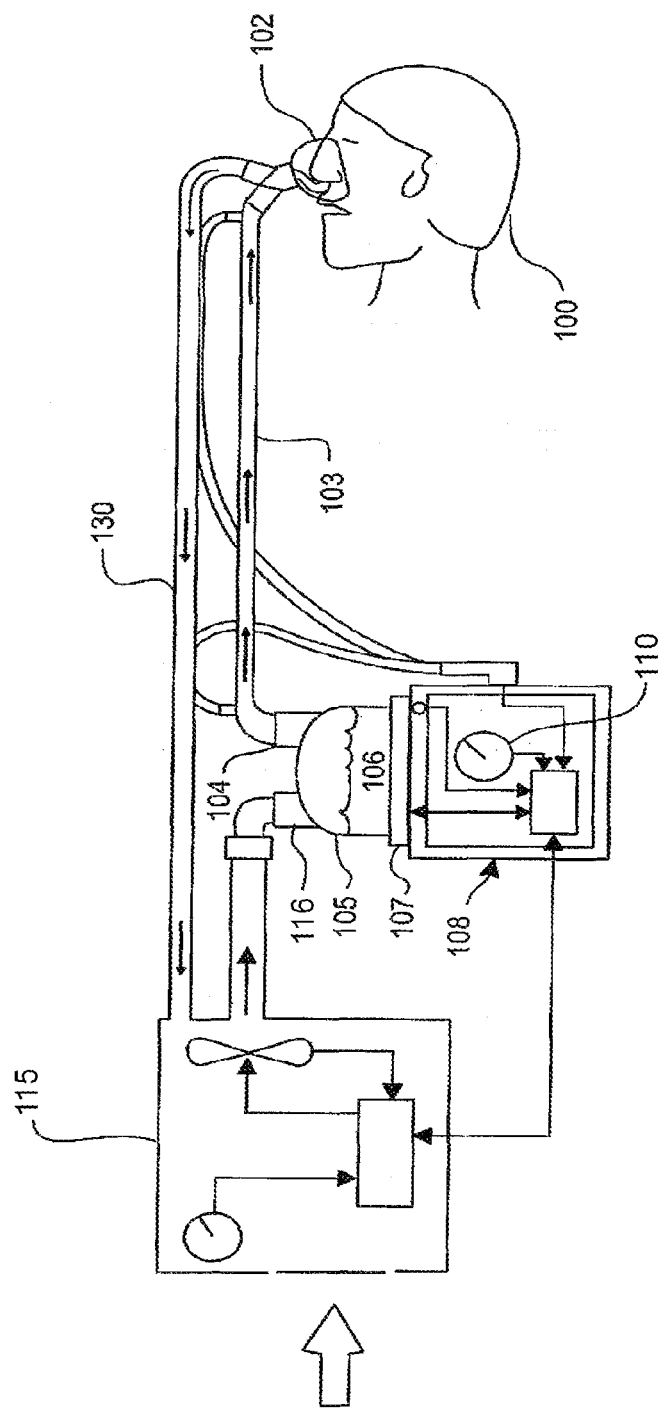
FIG. 1 is a schematic illustration of one type of breathing circuit in which a component according to the invention may be used.

In the field of medical circuits, and particularly in the field of breathing circuits (including anaesthetic circuits), condensation or rain-out can be a particular problem where high humidity breathing gases come into contact with the walls of a component at a relatively lower temperature. With reference to FIG. 1, a humidified ventilation system is shown in which a patient 100 is receiving humidified and pressurised gases through a patient interface 102 connected to a humidified gases transportation pathway or inspiratory breathing tube 103. It will be appreciated the patient interface 102 may take the form of a nasal mask, oral mask, oronasal mask, nasal prongs, endotracheal tube or full-face mask, etc.

It should be understood that delivery systems also could be continuous, variable or bi-level positive airway pressure or numerous other forms of respiratory therapy. The inspiratory breathing tube 103 is connected to an outlet 104 of a humidification chamber 105, which contains a volume of water 106. The inspiratory breathing tube 103 may include a heater or heater wires (not shown) that heat the humidified gases within the tube to reduce the formation of condensation. The humidification chamber 105 is heated by a heater plate 107 of a humidifier base 108. The humidifier base 108 can be connected to an electronic controller, which may comprise a microprocessor-based controller executing computer software commands stored in associated memory.

In response to a user set humidity or temperature value, which value can be input via a dial 110, for example but without limitation, and/or other inputs, the controller determines when (or to what level) to energise the heater plate 107 to heat the water 106 within the humidification chamber 105. As the volume of water is heated, water vapour begins to fill the chamber above the water's surface and is passed out of the humidification chamber outlet 104. A flow of gases (for example air) is provided from a gases supply or ventilator 115, which flow of gases enters the humidification chamber 105 through an inlet 116. Exhaled gases from the patient's mouth are returned to the ventilator through a return expiratory breathing tube 130, which expiratory breathing tube 130 may also include a heater or heater wires (not shown) that heat the humidified gases within the expiratory breathing tube 130 to reduce the formation of condensation.

It is preferable that the medical tubing (for example, the inspiratory and/or expiratory breathing tubes 103,130) is: (1) substantially resistant to crushing; (2) substantially resistant to restrictions in flow when bent (increased resistance to flow <50% when bent around a 1 inch cylinder); (3) substantially resistant to kinking; (4) substantially resistant to changes in length/volume under fluctuating internal pressure (i.e., resistant to compliance); (5) substantially resistant to leaking (i.e., leakage of <25 ml/min @6 kPa); (6) low in flow resistance (i.e., an increase in pressure @ max. rated flow <0.2 kPa); (7) substantially electrically safe (i.e., sparks minimized or eliminated in the tubing during use); and/or (8) of a single lumen design.

International standard ISO 5367:2000(E) (Fourth edition, 2000 Jun. 1) is one example of how some of these desirable parameters are measured and quantified, and the document is hereby incorporated into this specification in its entirety by reference. It is preferable that components of the invention meet or exceed some or all of these standards. Further, reference to medical tubes includes breathing tubes as defined in the above ISO standard.

According to one embodiment of the invention, there is provided a medical tube 200 comprising a tube wall 201 defining a passageway 203 for transportation of gas, and having a first end and a second end (such as, for example, a machine end and a patient end). The passageway 203 provides for fluid communication between the ends. At one (or both) end(s) of the medical tube there is provided a cuff 204 over-moulded about and attaching of one or more first pre-formed component(s) 205, one or more second pre-formed component(s) 206, and at least a portion of the at least one tube end 202. The cuff 204 is formed such that, in use, the first pre-formed component or components 205 is in fluid communication with the passageway 203, the one or more first pre-formed component 205 being configured for fluid connection with a further component(s) of a breathing circuit, and the second pre-formed component 206 being receivable of an auxiliary medical tube appliance (not shown).

The one or more first pre-formed component 205 can be formed or configured such that it may comply or be fittingly engageable with those connectors or fittings as required to comply with ISO 5356-1:2004 for 22 mm tapered connections.

Figure 2:
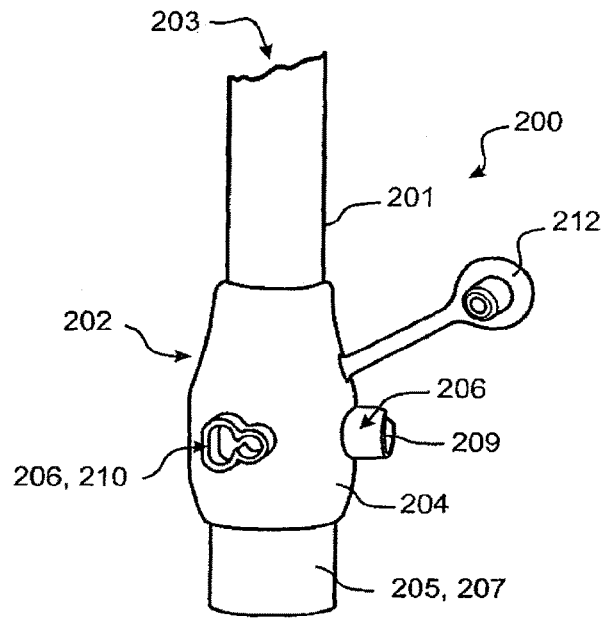
FIG. 2 illustrates a first embodiment of an end of a conduit according to the invention.

A tube end 202 of a conduit or medical tube 200 according to one embodiment of the invention is illustrated in FIG. 2. The medical tube 200 comprises a tube wall 201 defining the passageway (or lumen) 203 for transportation of breathing gases along the tube from a first end to a second end of the tube wall, for example from a machine end of the medical tube in fluid communication with a blower unit to a patient end of the conduit in fluid communication with a face mask or other patient interface. One or both ends of the medical tube 200 may be configured as illustrated in FIG. 2.

With reference to FIG. 2, and at a tube end 202 of the medical tube, the first pre-formed component 205 provides for a pneumatic port 207 in fluid communication with the passageway 203. The first pre-formed component 205 can be shaped or configured for connection with a further component of a breathing a circuit, for example to a humidification device (e.g. outlet from humidifier chamber) or a patient interface (e.g. mask or nasal cannula), or other connecting device.

Such a first pre-formed component 205 is pre-formed (or pre-moulded) prior to being over-moulded with the cuff 204. The first pre-formed component 205, for example, can be formed from a relatively rigid material for ease of connection with a further component of a breathing a circuit, including insufflator circuits, or alternatively for durability with re-use.

It will be appreciated the pneumatic port 207 preferably is substantially axially aligned with the passageway 203, or substantially aligned with the passageway 203 or tube wall 201, such that pneumatic (or fluid) connection between the pneumatic port 207 and the passageway 203 is facilitated. As illustrated in FIG. 2, the pneumatic port 207 can be a tubular body having a longitudinal axis, such as a substantially cylindrical housing.

According to the first embodiment, the tube end 202 further comprises a second pre-formed component 206. Such a second pre-formed component 206 is adapted to receive an auxiliary medical tube appliance. In the illustrated embodiment, the second preformed component 206 is a port for receiving an auxiliary medical tube appliance (not shown).

For example, the auxiliary medical tube appliance can be a sensor (not shown) for sensing one or more characteristics of gas in the passageway. Accordingly, at least one of the second pre-formed components 206 comprises a sensor port 209 for receiving such a sensor. The second pre-formed component 206, for example, can be formed from a relatively rigid material for ease of connection with an auxiliary medical tube appliance, or alternatively for durability with re-use. Advantageously, the sensor port 209 is configured to position a sensor substantially perpendicular to a flow of gas in the passageway 203. The sensor received by the sensor port 209 advantageously may sense one or more characteristics of gas or gas flow in the passageway 203 (e.g., one or more of gas temperature, relative humidity, gas velocity, gas flow rate).

Figure 3:
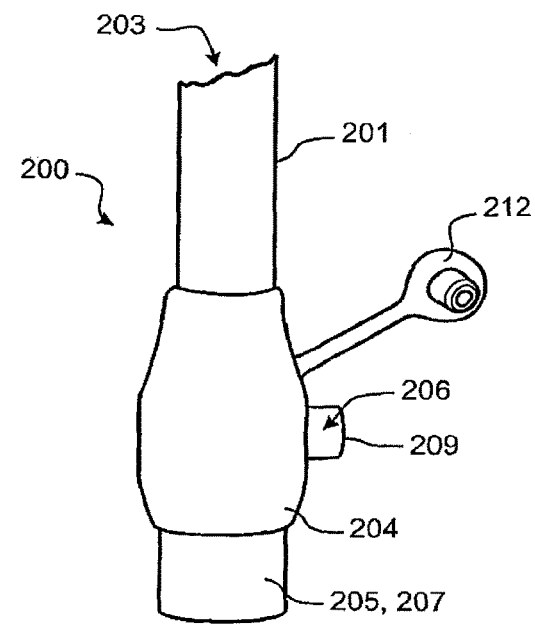
FIG. 3 illustrates a second embodiment of an end of a conduit according to the invention.
Figure 4:
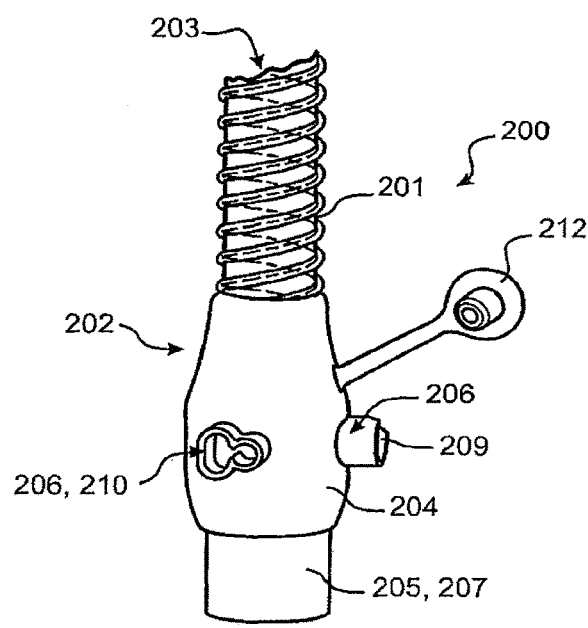
FIG. 4 illustrates a third embodiment of an end of a conduit according to the present invention.

In a preferred form, the auxiliary medical tube appliance is a temperature sensor that fittingly engages (e.g., fluidly seals) with the sensor port 209. FIGS. 2-5 illustrate embodiments of the medical tubes 200 comprising embodiments of the sensor port 209. FIGS. 2 and 4 illustrate configurations that additionally include an electrical port 210. A plug or cap 212 can provided for fluidly sealing the sensor port 209, although the plug or cap 212 could be appropriately shaped or configured for sealing the electrical port 210. In some configurations, at least one plug or cap 212 can be provided for both the sensor port 209 and the electrical port 210.

Figure 8:
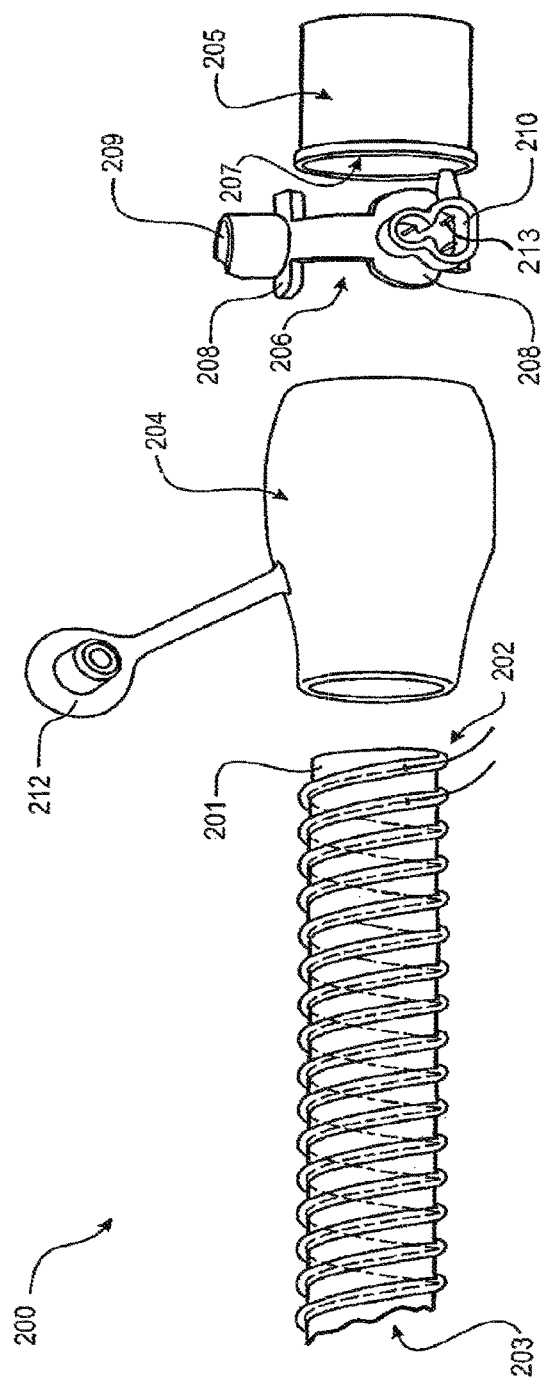
FIG. 8 illustrates, in exploded form, the separate parts forming a conduit end, according to the embodiments shown by FIG. 4.

In some configurations, the auxiliary medical appliance can be an electrical supply (e.g. a plug or electrical terminals) that is used to electrically connect a power source to the medical tube. Accordingly, at least one of the second pre-formed components 206 can comprise an electrical port 210 that is adapted to receive an electrical connector, for example providing an electrical supply to one or more electrically powered heater or heaters associated with the passageway 203. Advantageously, such a heater or heaters is/are located substantially within the passageway 203, or substantially within a tube wall 201 of the passageway 203, or substantially about an exterior surface of the passageway or tube wall 201. Such heaters may be one or more heater wires. Such electrically powered heaters may be electrically connected to terminals at the electrical port 210 via soldering of connections, or provision of suitable insulation displacement connector systems. FIGS. 2 and 4 illustrate embodiments of the medical tube 200 comprising a sensor port 209 and an electrical port 210. However, it will be appreciated an embodiment similar to that of any of the figures, including FIGS. 3 and 5, may be provided but where there is only an electrical port 210 and no sensor port 209 provided. Although not shown in FIGS. 2 and 4, the electrical port 210 preferably comprises electrical terminals, such as a set of pins 213 similar to those shown in electrical port 210 of FIG. 8.

Figure 9B:
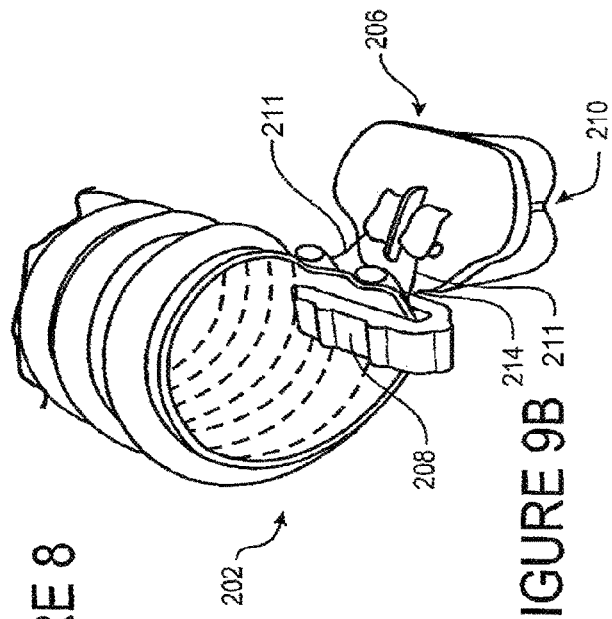
FIGS. 9A and 9B illustrate an alternative embodiment of locator clips associated with a second pre-formed component for connecting that component to the end of a conduit.
Figure 9A:
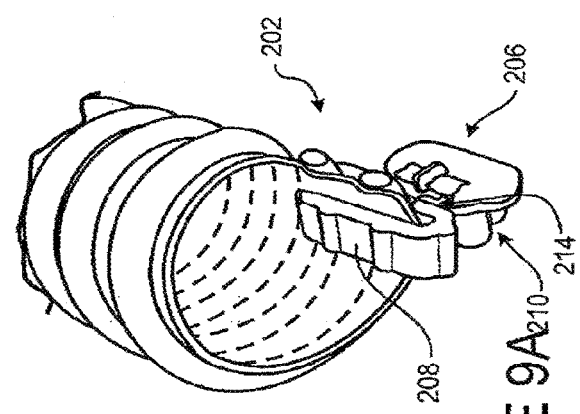

The electrical terminal connections of the electrical port 210 can be electrically connected to, for example, the heater wires 211 for completing an electrical circuit pathway. FIGS. 9A and 9B illustrate one example of electrical connections made between the heater wires 211 and the electrical terminals (e.g., pins 213) of the electrical port 210. FIGS. 9A and 9B further illustrate an embodiment of a locator 208 associated with the electrical port 210 attached to a region of one end of the medical tube 200. The electrical port 210, as shown by FIGS. 9A and 9B, may include a plastic hinge 214 (not specifically detailed) that allows the locator 208 and the electrical port 210 to be closed such that subsequent over-moulding by a cuff is facilitated to provide for an assembled medical tube 200 as shown by the other figures.

Turning to the second pre-formed component 206, such a component is attachable to at least a part or parts of the at least one tube wall end. In this respect, one or more locators 208 may extend from the second pre-formed component 206 for attachment to at least a part or parts of the tube end. The locator(s) 208 are attachable to a section or sections of a wall forming the passageway and the at least one end of the tube.

Figure 5:
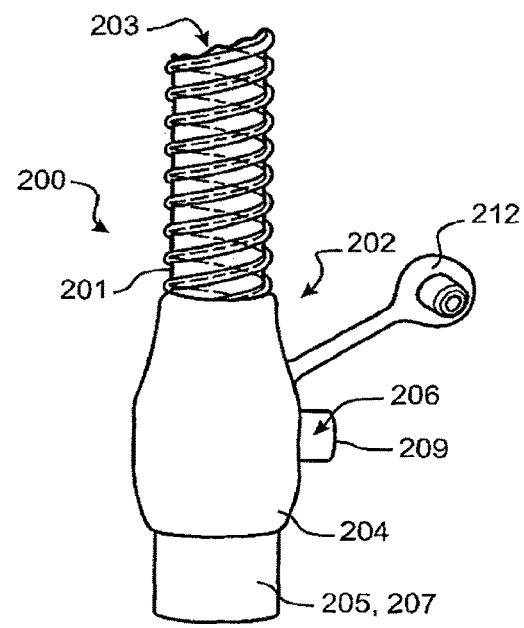
FIG. 5 illustrates a fourth embodiment of an end of a conduit according to the present invention.
Figures 6, 7A, 7B:
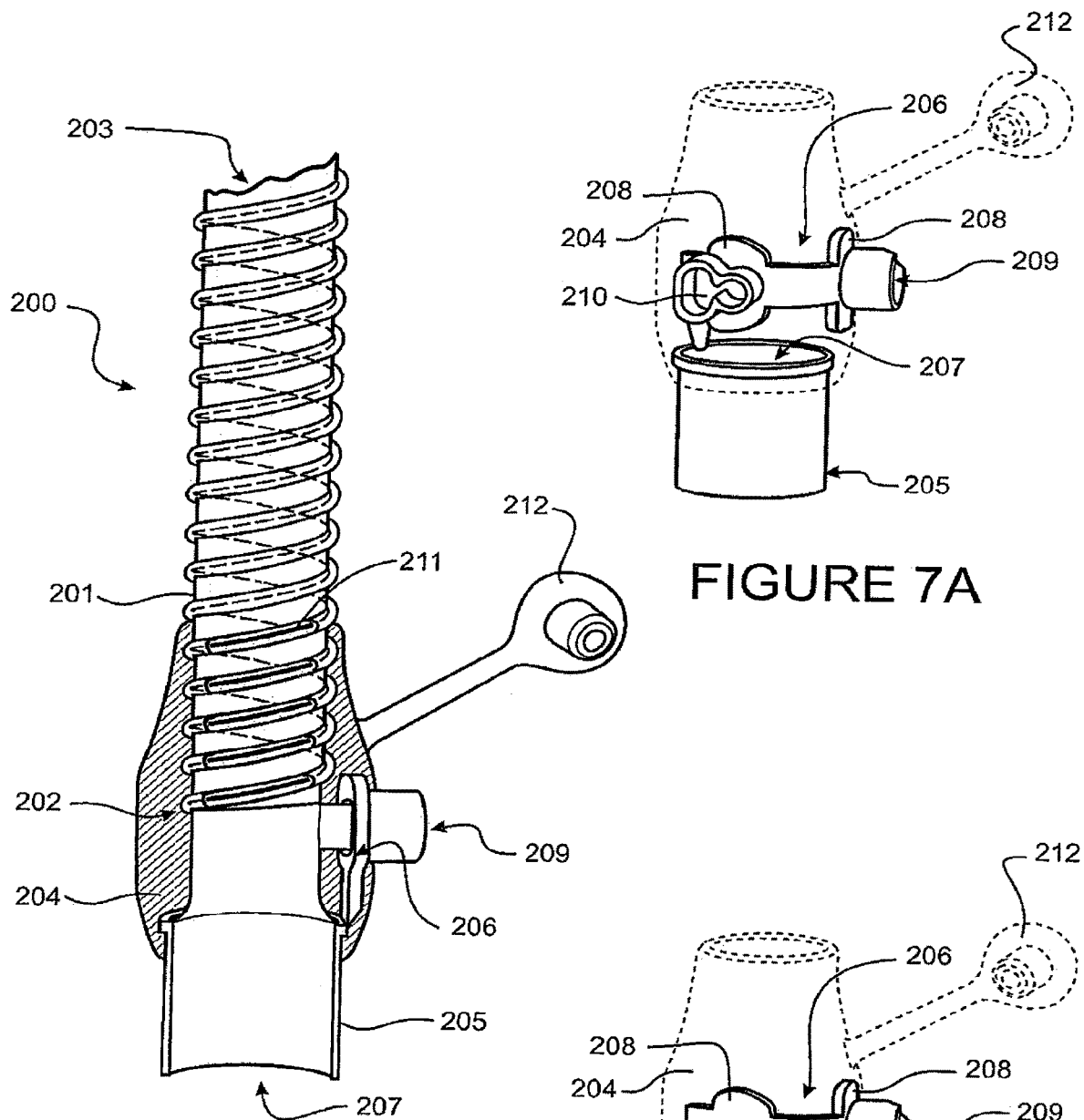
FIG. 6 is sectional view through an end of a conduit, for example through the end of FIG. 5.
FIG. 7A illustrates the relative location of a pre-formed first component and second pre-formed component, each of which are held in place by an over-moulded cuff (shown in phantom lines), according to the embodiment shown by FIG. 4.
FIG. 7B illustrates the relative location of a pre-formed first component and second pre-formed component, each of which are held in place by an over-moulded cuff (shown in phantom lines), according to the embodiment shown by FIG. 5.

In some configurations, the locators can be of a different form, such as that shown in FIGS. 9A and 9B, for example but without limitation. As shown by FIGS. 9A and 9B, the heater wires 211 contained within a helical bead extending about the outer surface of the conduit are exposed and are electrically terminated or connected to the electrical port 210. FIGS. 4 and 5 illustrate the medical tube 200 comprising a helical bead containing the electrically powered heater wire 211.

The at least one locator 208 of the second pre-formed component 206 can be employed for positioning the component in place relative to the end of the tube prior to over-moulding of the cuff 204. The second pre-formed component 206 is located longitudinally intermediate of the at least one end and the first pre-formed component 205. Such locators 208 may be a clip or clips for attaching or connecting to an end of the tube wall. However, such locators 208 may additionally provide further functionality.

For example, the one or more of the locators 208 may electrically connect the electrically powered heater or heaters associated with the passageway 203. In such a configuration, or other forms of this configuration, it will be appreciated the second pre-formed component 206 with an electrical port 210 allow for electrical connection of a power source to the heaters (e.g. heater wires).

The electrical connection can be by way of soldering of heater wires to the electrical terminal (e.g. pins in electrical port 210), or for example by insulation displacement connection of the locator clips to the heater wires, thereby creating an electrical pathway to the electrical terminal of the electrical port 210.

It will be appreciated the electrical port 210 is configured for providing electrical connection between an auxiliary medical appliance and those parts of the medical tube 200 needing electrical power for operation.

Figure 10A:
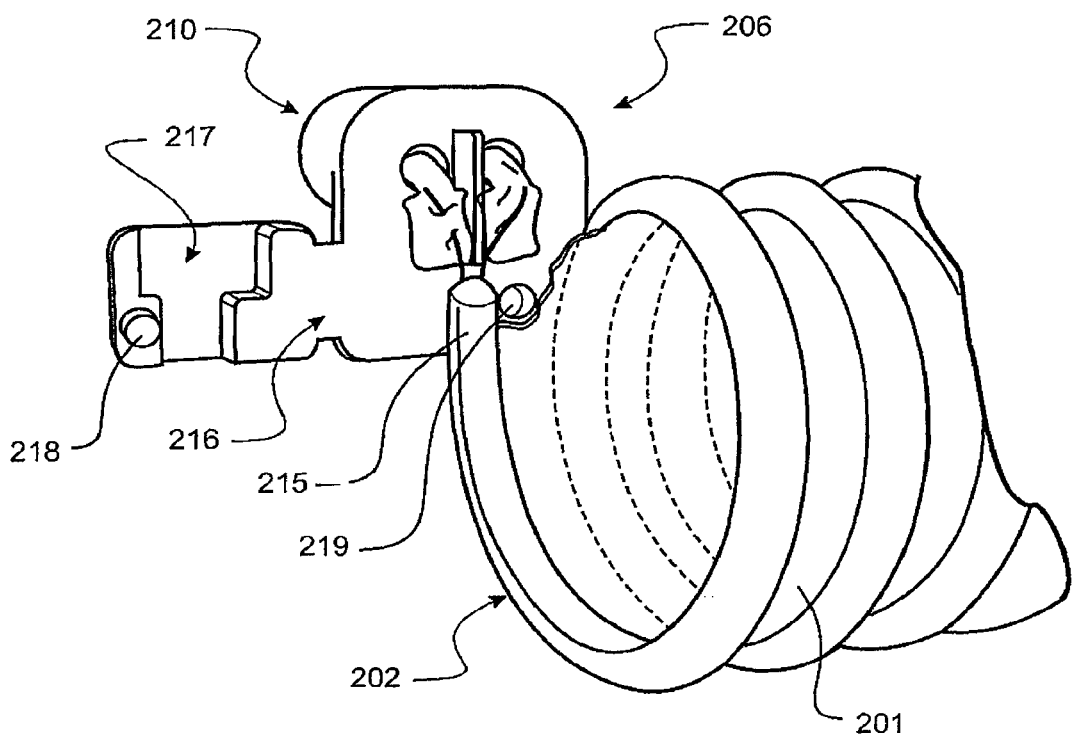
FIGS. 10a and 10b illustrate a further embodiment of a second pre-formed component for connecting that component to the end of a conduit, FIG. 10a illustrating the component in an "open" position, and FIG. 10b illustrating the component in a "closed" position.
Figure 10B:
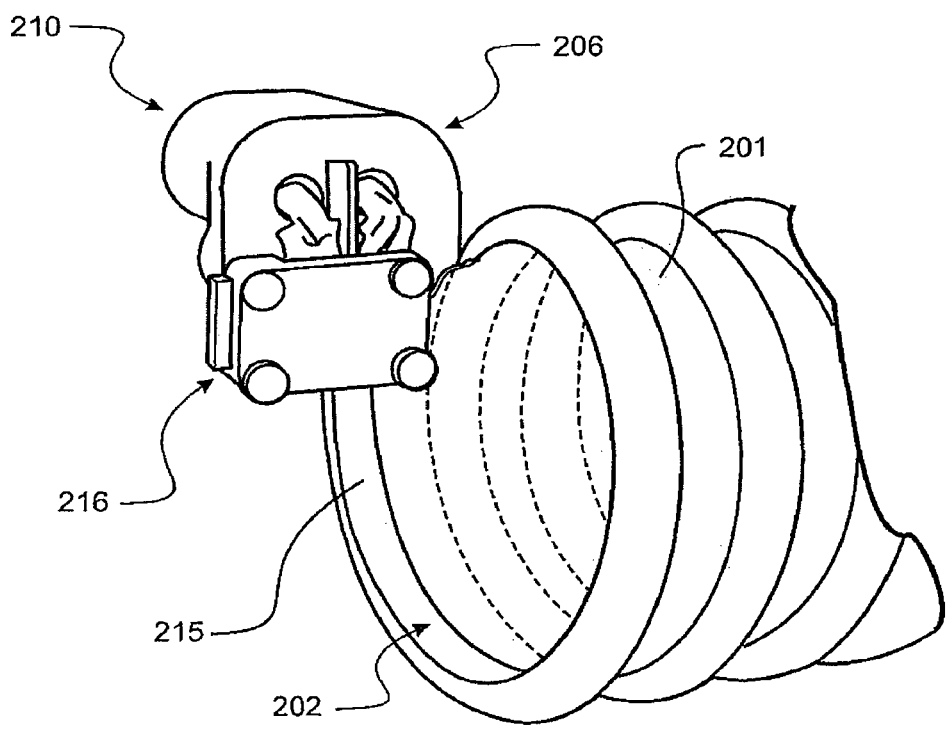

FIGS. 10a and 10b illustrate yet a further embodiment of how a second pre-formed component 206 may configured. Such a second pre-formed component 206 in these figures is shown, for the sake of clarity, without the optional sensor port 209 or the first pre-formed component 205, or the cuff 204 which is over-moulded. According to such an embodiment, the second pre-formed component 206 attaches to at least a portion of parts of the at least one tube end 202. Such a portion of parts that the second pre-formed component 206 attaches to may be a portion of a bead or rib or corrugated portion of a tube wall 201. An optional sensor port may be provided by such a second pre-formed component 206.

For example, the second pre-formed component 206 may attach to a bead 215. Such a bead 215 can encapsulate or house or locate a heater or heater wire or other electrical components (whether singular components or plural components) requiring electrical connection with an auxiliary medical tube appliance which can be connected to the electrical terminals of electrical port 210 (not specifically shown in FIG. 10a or 10b, but shown in FIGS. 2, 4, 7A, 8 by way of example).

In respect of such a further embodiment, the second pre-formed component 206 can be formed in a manner that allows the component to fold over upon itself. Such folding may be about a thinned mid-line or other region 216 of the second pre-formed component 206. In such a setup, the second pre-formed component 206 may advantageously provide for an appropriately shaped channel region 217 allowing for a pathway of electrical heaters or sensor wires or other electrical components extending from the end of the tube to the electrical terminals of the second pre-formed component 206.

Additionally, a latching arrangement comprising a protrusion 218 and a complimentary receptacle 219 for the protrusion may be provided for retaining the component in a folded arrangement. This may be provided in the form of a snap-fit or friction-fit positioning of the protrusion into the receptacle. It will however be appreciated that other forms of retention of the component in a folded arrangement may be contemplated.

Preferably, the second pre-formed component 206 provides for a secure retention between the component and at least a part or parts of the end of the tube.

The second pre-formed component 206 as shown by FIG. 10a and 10b may additionally provide for an improved security or latching region about electrical connections or solder joints, thereby protecting such connections or joints from impact or potential for fracture. Such a second pre-formed component 206 may facilitate improved stability of attachment or grip to the tube end 202 of the medical tube 200.

As shown by FIG. 10a, the second pre-formed component 206 is in an "open" position where the first part (e.g., the part housing the electrical port 210 or any sensor port (not shown)) of the component and its rear surface is exposed, showing electrical connection between heater wires extending from a tube bead and connecting to the electrical terminals of electrical port 210. The second part of the component (e.g., the part shown in this embodiment as having the channel region 217 and the protrusion 218) has the folding region or thinned region 216 allowing folding of the first and second parts together for retention of the second pre-formed component 206 to the tube end.

FIG. 10b shows the second pre-formed component 206 where the first and second parts are in a closed configuration and the second pre-formed component 206 is in retention of the tube. In the closed position, the protrusion 218 is received by the recess 219, such receipt providing for holding the component in its closed position.

In other forms, the second pre-formed component 206 is adapted to receive auxiliary medical appliances, where both of a sensor port 209 and an electrical port 210 are provided. Such a second pre-formed component 206 can be a single component or piece.

As shown in FIG. 2, the cuff 204 is over-moulded about and attaches to the first pre-formed component 205 and the second pre-formed component 206 and the at least one tube end 202 of the medical tube's wall 201 so that the first preformed component 205 is in fluid communication with the passageway 203. The cuff 204 is over-moulded in a single over-moulding operation or procedure. That is, there is no requirement for multiple moulding stages or sequences. Furthermore, there is no need for a protective layer, material or other shroud to cover or provide protection to the medical tube (particularly the wall of the tube) from the over-moulding material. Problems encountered in the past with over-moulding have included burn-through or melting of tube walls when cuff material is applied in a moulding condition (e.g. melt state).

The cuff 204 advantageously is formed of a material relatively more pliable than that of the first pre-formed component(s) and/or second pre-formed component(s), or may be of a material having a lower relative melting point than that of the first and second pre-formed component(s) 205, 206, and the material forming the tube wall 201.

Where the cuff material has a lower melting point than that of the material forming the tube wall 201, the cuff 204 can be directly attached during an over-moulding operation to an exterior surface of at least one end of the tube wall. As used herein, "directly attached" means the tube end 202 does not comprise any intermediate layer or protective collar or material positioned between the cuff 204, which is over-moulded, and an exterior surface of the tube wall 201, such as for preventing direct contact between the over-moulded cuff and the exterior surface of the tube wall.

The cuff 204, which is over-moulded, forms a pneumatic seal about at least one tube wall end and between the first pre-formed component(s) 205 and the second pre-formed component(s) 206, whilst maintaining fluid connection between the first pre-formed component(s) 205 and the at least one tube end 202 and passageway 203 of the medical tube 200.

In another form, the cuff 204 can optionally include one or more caps or plugs 212. Such a cap or plug 212 can be utilised to cap or plug a sensor port 209 or an electrical port 210 when either (or both) are not in use, or do not have an auxiliary appliance in-situ. Such a plug 212 may further ensure a pneumatic seal is provided between the passageway and the pneumatic port 207 or end of the first pre-formed component 205 when one or more of the sensor port 209 or electrical port 210 is provided but no auxiliary appliance is positioned therein.

An alternative conduit end to that illustrated in FIG. 2 is an end that comprises more than one first pre-formed component 205 (e.g., may have two or more pneumatic ports) or more than one second pre-formed component 206 (e.g., may have separate second pre-formed components 206 providing for separate sensor port 209 and separate electrical port 210). In yet an even further alternative, as previously described, and as illustrated by FIG. 3, there may be provided only a sensor port 209 with no electrical port. It will be appreciated such a configuration may be in the alternative, that is, an electrical port 210 may be provided, but no sensor port.

As shown in FIGS. 2 and 3, the interior wall surface of the medical tube may be substantially smooth or of an undefined shape. In some configurations, such as illustrated in FIGS. 4 and 5 for example, the tube wall 201 can comprise a rib formed in or on the tube wall of the conduit. As illustrated the rib can be helically disposed along the length of the tube wall 201. Separate ribs may be formed spaced apart along the length of the tube wall. For example, a separate rib may be formed around a circumference of the tub wall and may be linearly spaced apart from further separate ribs. Such ribs may be utilised for structural strength purposes of the medical tube, or may encapsulate, overlie or surround an electrically powered heater, for example a heater wire, or may provide both a heater encapsulation and a tube strength benefit.

In some embodiments, the interior wall surface of the passageway may be a smooth surface. In various embodiments, the interior of the passageway may be devoid of corrugations, convolutions or undulations. Such a configuration may assist with the ability to clean medical tubing for re-use. In some embodiments, the passageway of the tube wall comprises a corrugated form, although this may be less preferable for ease of cleaning for subsequent re-use. In re-use applications, the medical tube, or at least the interior surface of the passageway of the medical tube, advantageously is mechanically and/or chemically cleanable. Preferably, at least those surfaces of the medical tube that are in contact with the gas (i.e., inspiratory or expiratory limbs) can be mechanically and/or chemically cleanable.

In some embodiments, the medical tube 200 comprises a tube wall defining a passageway 203 for transportation of gas, and having a first end and a second end (such as, for example, a machine end and a patient end). The passageway 203 provides for fluid communication between the ends and at least one tube end 202 of the medical tube 200 comprises a pre-formed pneumatic port component in fluid communication with the passageway. The component can be configured for fluid connection with a further component(s) of a breathing circuit. A pre-formed sensor port component is receivable of a sensor for sensing one or more characteristics of gas in the passageway 203 and a cuff 204 is over-moulded about and thereby connects the pneumatic port component, the sensor port component and at least a portion of the tube end. In some embodiments, at least one tube end further comprises a pre-formed electrical port component receivable of an electrical connection for providing an electrical circuit or pathway to one or more electrical appliances associated with the passageway, the cuff being additionally over-moulded over the pre-formed electrical port component.

In some embodiments, the medical tube 200 comprises a tube wall defining a passageway for transportation of gas and having a first end and a second end (such as, for example, a machine end and a patient end). The passageway provides for fluid communication between the ends and at least one end of the medical tube comprises a pre-formed pneumatic port connector component in fluid communication with the passageway. The connector component can be configured for fluid connection with a further component(s) of a breathing circuit. A pre-formed electrical port component can be receivable of an electrical connection for providing an electrical circuit or pathway to one or more electrical appliances associated with the passageway. A cuff can be over-moulded about and can thereby connect the pneumatic port component, the electrical port component and at least a portion of the tube end. In some configurations, at least one tube end further comprises a pre-formed sensor port component receivable of a sensor for sensing one or more characteristics of gas in the passageway, the cuff being additionally over-moulded over the pre-formed sensor port component.

In respect of the embodiments above, the pneumatic port is generally as shown by the first pre-formed component 205 as previously described; the sensor port component is generally as shown by the second pre-formed component part 206 as previously described; and the electrical port component is generally as shown by the second pre-formed component part 206. Notably, an electrical port 210 and a sensor port 209 may each be optionally included in such arrangements of medical tubes 200. Where an electrical port is provided, various forms of electrical connection and electrically powered heater or heaters, as previously described, can be implemented. Likewise, where a sensor port is provided, various forms of the sensor port and sensor positioning, as previously described, can be implemented.

In constructing the medical tubes 200 of the various embodiments above, one such method for fabrication comprises one or more of the following steps:

soldering heater wires together at the patient end of the tube to form a closed electrical circuit, providing a length of tube, the length of tube comprising a tube wall defining a passageway for transportation of gas, and having a first end and a second end (e.g., a machine end and a patient end), the passageway providing for fluid communication between the ends, locating one or more first pre-formed component or components substantially adjacent at least one of the ends of the tube, inserting or providing electrical contact pins in the pre-formed component comprising the electrical port for establishing an electrical connection between an auxiliary medical appliance providing power to those parts of the tube requiring electrical power (e.g., heater wire), attaching the machine end of the tube to the electrical port component and soldering or connecting the heater wires from the tube to the electrical contact pins, keeping the heater wires on the external surface of the tube in a single over-moulding procedure, over-moulding a cuff about the first pre-formed component(s), the second pre-formed component(s) and at least a portion of the ends of the tube, the over-moulded cuff attaching to and locating the pre-moulded component(s) in place relative to the at least one end of the tube such that, in use, the first pre-formed component or components is in fluid communication with the passageway, the, or each, first pre-formed component configured for fluid connection with a further component(s) of a breathing circuit, and the second pre-formed appliance component or components is receivable of a tube appliance.

In some methods, the steps also may optionally provide for the electrical port to be located on the outside of the cuff and electrically connected to the tube's heater wires such that there are no bare heater wires on the interior surface of the tube. Such a configuration may have particular application in improving safety of such electrically powered tubes.

Such a fabrication can be performed using a mould receivable of the at least one tube end 202, as well as the various pre-formed components (205, 206). For example, in a moulding die:

the at least one end of the tube is positioned in a tube receiving mould position, the first pre-formed component(s) is/are positioned in first pre-formed component receiving mould position, the second pre-formed component(s) is/are positioned in a second pre-formed component receiving mould position, the electrical contact pins are connected to the tube heater wires and positioned in the relevant mould position, such that, the cuff is formed by over-moulding a moulding material about each of the pre-formed components and at least a portion of the at least one end of the tube.

Tube materials may be those chosen to be suitable for re-use applications, for durability, for hygiene or sterility purposes, as well as for complying with standards governing breathing tubes.

The foregoing description of the invention includes preferred forms thereof. Modifications may be made thereto without departing from the scope of the invention.

Preferred Features

1b. A medical tube comprising:

a tube wall defining a passageway for transportation of gas, and having a first end and a second end (such as, for example, a machine end and a patient end), the passageway providing for fluid communication between the ends, wherein at least one end of the medical tube comprises:

a pre-formed pneumatic port component in fluid communication with the passageway, the component configured for fluid connection with a further component(s) of a breathing circuit, a pre-formed sensor port component receivable of a sensor for sensing one or more characteristics of gas in the passageway, and a cuff over-moulded about and connecting of the pneumatic port component, sensor port component and at least a portion of the tube end.

2b. The tube as recited in paragraph 1b, wherein the sensor port component is arranged such that a sensor located by the sensor port component is in fluid communication with the passageway and positioned to be substantially perpendicular to flow of gas in the passageway.

3b. The tube as recited in paragraph 1b or paragraph 2b, wherein a sensor receivable by the sensor port component is sensing of one or more of gas temperature, relative humidity, gas velocity (or flow rate).

4b. The tube as recited in any one of paragraphs 1b to 3b, wherein the sensor is fluidly connected to or in fluid connection with the passageway.

5b. The tube as recited in any one of paragraphs 1b to 4b, wherein the pre-formed sensor port component comprises at least one locator for attachment to at least a section of a wall forming the passageway or the at least one end of the tube.

6b. The tube as recited in any one of paragraphs 1b to 5b, wherein the at least one tube end further comprises a pre-formed electrical port component receivable of an electrical connection for providing an electrical circuit or pathway to one or more electrical appliances associated with the passageway, the cuff being additionally over-moulded of the pre-formed electrical port component.

7b. The tube as recited in paragraph 6b, wherein the electrical appliance is at least one electrically powered heater associated with the passageway of the tube.

8b. The tube as recited in paragraph 7b, wherein the heater is located substantially within the passageway, or substantially within a wall of the passageway, or substantially about an exterior surface of the passageway.

9b. The tube as recited in paragraph 7b or paragraph 8b, wherein the heater is located substantially about an exterior surface of the passageway.

10b. The tube as recited in any one of paragraphs 7b to 9b, wherein the heater is a heat source for gas passing through the passageway.

11b. The tube as recited in any one of paragraphs 7b to 10b, wherein the heater is at least one heater wire.

12b. The tube as recited in any one of paragraphs 6b to 11b, wherein the pre-formed electrical port component comprises at least one locator for attachment to at least a section of a wall forming the passageway or the at least one end of the tube.

13b. The tube as recited in paragraph 12b, wherein the at least one locator comprises electrical connector(s) for electrically coupling the electrical connector with one or more electrically powered heater or heaters associated with the passageway.

14b. The tube as recited in any one of paragraphs 6b to 13b, wherein the electrical port is fluidly sealed from communication with the passageway.

15b. The tube as recited in any one of paragraphs 6b to 14b, wherein the pre-formed sensor port component and pre-formed electrical port component are a single pre-moulded component.

16b. The tube as recited in any one of paragraphs 1b to 15b, wherein the over-moulded cuff forms a pneumatic seal about, at least, the at least one tube end and between the pre-formed pneumatic component and the pre-formed sensor port component, whilst maintaining fluid connection between the pre-formed pneumatic port component and the at least one end of the tube and passageway.

17b. The tube as recited in any one of paragraphs 1b to 16b, wherein the cuff is directly attached during an over-moulding operation to, at least, an exterior surface of the at least one end of the tube, the pre-formed sensor port and the pre-formed pneumatic port.

18b. The tube as recited in any one of paragraphs 1b to 17b, wherein the cuff is formed from, or by, a single over-moulding procedure.

19b. The tube as recited in any one of paragraphs 1b to 18b, wherein no intermediate layer or protective collar or material is positioned between, at least, the over-moulded cuff and an exterior wall of the passageway, such as for preventing direct contact between the over-moulded cuff and the exterior wall of the passageway.

20b. The tube as recited in any one of paragraphs 1b to 19b, wherein the cuff is formed of a material having a lower relative melting point than that of, at least, the pre-formed pneumatic port component, the pre-formed sensor port component, and material forming a wall of the passageway.

21b. The tube as recited in any one of paragraphs 1b to 19b, wherein the cuff is formed of a material relatively more pliable than that of, at least, the pre-formed pneumatic port component and/or the pre-formed sensor port component.

22b. The tube as recited in any one of paragraphs 1b to 21b, wherein the pre-formed sensor port component is located longitudinally intermediate of the at least one end and the pre-formed pneumatic port component.

23b. The tube as recited in any one of paragraphs 1b to 22b, wherein the pre-formed pneumatic port component is substantially axially aligned with the tube passageway, and/or the pre-formed pneumatic port component is substantially aligned with the tube passageway such that pneumatic connection between the pre-formed pneumatic port component and the passageway is provided.

24b. The tube as recited in any one of paragraphs 1b to 23b, wherein the interior of the passageway is of a smooth linear surface.

25b. The tube as recited in any one of paragraphs 1b to 24b, wherein the interior of the passageway is devoid of corrugations, convolutions or undulations.

26b. The tube as recited in any one of paragraphs 1b to 23b, wherein the wall is of a corrugated form.

27b. The tube as recited in any one of paragraphs 1b to 26b, wherein the interior surface of the passageway is mechanically and/or chemically cleanable, and/or surfaces in contact with the gas is mechanically and/or chemically cleanable.

28b. The tube as recited in any one of paragraphs 1b to 27b, wherein the tube is a reusable medical tube.

1c. A medical tube comprising:
a tube wall defining a passageway for transportation of gas, and having a first end and a second end (such as, for example, a machine end and a patient end), the passageway providing for fluid communication between the ends,
wherein at least one end of the medical tube comprises:
a pre-formed pneumatic port connector component in fluid communication with the passageway, the connector component configured for fluid connection with a further component(s) of a breathing circuit,
a pre-formed electrical port component receivable of an electrical connection for providing an electrical circuit or pathway to one or more electrical appliances associated with the passageway, and
a cuff over-moulded about and connecting of the pneumatic port component, electrical port component and at least a portion of the tube end.

2c. The tube as recited in paragraph 1c, wherein the electrical appliance is at least one electrically powered heater associated with the passageway of the tube.

3c. The tube as recited in paragraph 2c, wherein the heater is located substantially within the passageway, or substantially within a wall of the passageway, or substantially about an exterior surface of the passageway.

4c. The tube as recited in paragraph 2c or paragraph 3c, wherein the heater is located substantially about an exterior surface of the passageway.

5c. The tube as recited in any one of paragraphs 2c to 4c, wherein the heater is a heat source for gas passing through the passageway.

6c. The tube as recited in any one of paragraphs 2c to 5c, wherein the heater is at least one heater wire.

7c. The tube as recited in any one of paragraphs 1c to 6c, wherein the pre-formed electrical port component comprises at least one locator for attachment to at least a section of a wall forming the passageway or the at least one end of the tube.

8c. The tube as recited in paragraph 7c, wherein the at least one locator comprises electrical connector(s) for electrically coupling the electrical connector with one or more electrically powered heater or heaters associated with the passageway.

9c. The tube as recited in any one of paragraphs 1c to 8c, wherein the electrical port is fluidly sealed from communication with the passageway.

10c. The tube as recited in any one of paragraphs 1c to 9c, wherein the at least one tube end further comprises a pre-formed sensor port component receivable of a sensor for sensing one or more characteristics of gas in the passageway, the cuff being additionally over-moulded of the pre-formed sensor port component.

11c. The tube as recited in paragraph 10c, wherein the sensor port component is arranged such that a sensor located by the sensor port component is in fluid communication with the passageway and positioned to be substantially perpendicular to flow of gas in the passageway.

12c. The tube as recited in paragraph 10c or paragraph 11c, wherein a sensor receivable by the sensor port component is sensing of one or more of gas temperature, relative humidity, gas velocity (or flow rate).

13c. The tube as recited in any one of paragraphs 10c to 12c, wherein the sensor is fluidly connected to or in fluid connection with the passageway.

14c. The tube as recited in any one of paragraphs 10c to 13c, wherein the pre-formed sensor port component comprises at least one locator for attachment to at least a section of a wall forming the passageway or the at least one end of the tube.

15c. The tube as recited in any one of paragraphs 10c to 14c, wherein the sensor port and electrical port are a single pre-moulded component.

16c. The tube as recited in any one of paragraphs 1c to 15c, wherein the over-moulded cuff forms a pneumatic seal about, at least, the at least one tube end and between the pre-formed electrical port component and the pre-formed pneumatic port component, whilst maintaining fluid connection between the pneumatic port and the at least one end of the tube and passageway.

17c. The tube as recited in any one of paragraphs 1c to 16c, wherein the cuff is directly attached during an over-moulding operation to an exterior surface of the at least one end of the tube.

18c. The tube as recited in any one of paragraphs 1c to 17c, wherein the cuff is directly attached to, at least, the pre-formed pneumatic port component, pre-formed electrical port component during an over-moulding procedure.

19c. The tube as recited in any one of paragraphs 1c to 18c, wherein the cuff is formed from or by a single-step over-moulding procedure.

20c. The tube as recited in any one of paragraphs 1c to 19c, wherein the pre-formed pneumatic port component provides for pneumatic connection with the at least one end of the passageway.

21c. The tube as recited in any one of paragraphs 1c to 20c, wherein the pre-formed pneumatic port component is substantially axially aligned with the tube passageway and/or wherein the pre-formed pneumatic port component is substantially aligned with the tube passageway such that pneumatic connection between the pre-formed pneumatic port component and the passageway is provided.

22c. The tube as recited in any one of paragraphs 1c to 21c, wherein the cuff is formed of a material having a lower relative melting point than that of, at least, the pneumatic port component, electrical port component, and passageway.

23c. The tube as recited in any one of paragraphs 1c to 22c, wherein the cuff is formed of a material that is relatively more pliable that that of, at least, the pneumatic port component, electrical port component, and passageway.

24c. The tube as recited in any one of paragraphs 1c to 23c, wherein the interior of the passageway is of a smooth linear surface.

25c. The tube as recited in any one of paragraphs 1c to 24c, wherein the interior of the passageway is devoid of corrugations, convolutions or undulations.

26c. The tube as recited in any one of paragraphs 1c to 23c, wherein the wall is of a corrugated form.

27c. The tube as recited in any one of paragraphs 1c to 26c, wherein the interior surface of the passageway is mechanically and/or chemically cleanable, and/or surfaces in contact with the gas is mechanically and/or chemically cleanable.

28c. The tube as recited in any one of paragraphs 1c to 27c, wherein the tube is a reusable medical tube.

What is claimed is:

1. A medical comprising:
   a tube wall defining a passageway for transportation of gas and having a first end and a second end, the passageway providing for fluid communication between the first end and the second end,
   wherein at least one of the first end and the second end comprises:
   a cuff over-moulded about one or more first preformed components, one or more second preformed components, and at least a portion of the tube wall, wherein at least a portion of an interior surface of the cuff is in fluid communication with the passageway,
   such that in use, the one or more first preformed components are in fluid communication with the passageway, the one or more first preformed components configured for fluid connection with one or more further components of a breathing circuit, and the one or more second preformed components are receivable of one or more auxiliary medical tube appliances,
   wherein the one or more first preformed components and the one or more second preformed components are formed from a relatively rigid material, and
   wherein the cuff is formed of a material relatively more pliable than that of the one or more first preformed components and the one or more second preformed components.

2. The medical tube of claim 1, wherein the one or more first preformed components are spaced apart from the at least a portion of the tube wall along a longitudinal axis of the medical tube to form a gap therebetween, and wherein the cuff extends across the gap and connects the one or more first preformed components and the tube wall.

3. The medical tube of claim 1, wherein the one or more first preformed components comprises a pneumatic port, the pneumatic port providing for pneumatic connection with the at least one of the first end and the second end of the tube wall.

4. The medical tube of claim 1, wherein the one or more second preformed components comprises one or more locators extending from the one or more second preformed components for attachment to the at least one of the first end and the second end of the tube wall.

5. The medical tube of claim 1, wherein the one or more second preformed components comprises a port, the port receivable of the one or more auxiliary medical tube appliances.

6. The medical tube of claim 1, wherein the one or more auxiliary medical tube appliances is a sensor for sensing one or more characteristics of gas in the passageway.

7. The medical tube of claim 1, wherein the one or more second preformed components comprises a sensor port, the sensor port receivable of a sensor for sensing one or more characteristics of gas in the passageway.

8. The medical tube of claim 1, wherein the one or more auxiliary medical tube appliances is an electrical supply for one or more electrically powered heaters associated with the passageway.

9. The medical tube of claim 1, wherein the cuff forms a pneumatic seal about the at least one of the first end and the second end of the tube wall and between the one or more first preformed components and the one or more second preformed components, whilst maintaining fluid connection between the one or more first preformed components and the at least one of the first end and the second end of the tube wall.

10. The medical tube of claim 1, wherein no intermediate layer is positioned between the cuff and the at least a portion of the tube wall, such as for preventing direct contact between the cuff and the at least portion of the tube wall.

11. The medical tube of claim 1, wherein the cuff is formed of a material having a lower relative melting point than the material of the one or more first preformed components, the one or more second preformed components, and the tube wall.

12. The medical tube of claim 1, wherein at least a portion of the one or more second preformed components is located longitudinally intermediate of the at least one of the first end and the second end of the tube wall and the one or more first preformed components.

13. The medical tube of claim 1, wherein the one or more first preformed components are substantially axially aligned with the passageway such that pneumatic connection between the one or more first preformed components and the passageway is provided.

14. The medical tube of claim 1, wherein the one or more second preformed components comprises a sensor port and an electrical port as a single pre-moulded component.

15. The medical tube of claim 1, wherein an interior of the passageway is of a smooth linear surface.

16. The medical tube of claim 1, wherein the one or more second preformed components comprises an electrical port, the electrical port receivable of an electrical connector for providing an electrical supply to one or more electrically powered heaters associated with the passageway.

17. The medical tube of claim 16, wherein the one or more electrically powered heaters are located substantially within the passageway.

18. The medical tube of claim 16, wherein the one or more electrically powered heaters are located substantially about an exterior surface of the tube wall.

19. The medical tube of claim 16, wherein the one or more electrically powered heaters are one or more heater wires.

20. A medical tube comprising:
a tube wall defining a passageway for transportation of gas and having a first end and a second end, the passageway providing for fluid communication between the first end and the second end,
wherein at least one of the first end and the second end comprises:
a preformed pneumatic port component in fluid communication with the passageway, the preformed pneumatic port component configured for fluid connection with one or more further components of a breathing circuit,
a preformed sensor port component receivable of a sensor for sensing one or more characteristics of gas in the passageway,
a cuff over-moulded about the preformed pneumatic port component, the preformed sensor port component and at least a portion of the tube wall,
wherein the preformed pneumatic port component and the preformed sensor port component are formed from a relatively rigid material, and
wherein the cuff is formed of a material relatively more pliable than that of the preformed pneumatic port component and the preformed sensor port component.

21. The medical tube of claim 20, wherein the preformed pneumatic port component is spaced apart from the at least a portion of the tube wall along a longitudinal axis of the medical tube to form a gap therebetween, and wherein the cuff extends across the gap and connects the preformed pneumatic port component and the tube wall.

22. A medical tube comprising:
a tube wall defining a passageway for transportation of gas and having a first end and a second end, the passageway providing for fluid communication between the first end and the second end,
wherein at least one of the first end and the second end comprises:
a preformed pneumatic port component in fluid communication with the passageway, the preformed pneumatic port component configured for fluid connection with one or more further components of a breathing circuit,
a preformed electrical port component receivable of an electrical connection for providing an electrical circuit to one or more electrical appliances associated with the passageway,
a cuff over-moulded about the preformed pneumatic port component, the preformed electrical port component and at least a portion of the tube wall,
wherein the preformed pneumatic port connector component and the preformed electrical port component are formed from a relatively rigid material, and
wherein the cuff is formed of a material relatively more pliable than that of the preformed pneumatic port component and the preformed electrical port component.

23. The medical tube of claim 22, wherein the preformed pneumatic port component is spaced apart from the at least a portion of the tube wall along a longitudinal axis of the medical tube to form a gap therebetween, and wherein the cuff extends across the gap and connects the preformed pneumatic port component and the tube wall.

* * * * *

UNITED STATES PATENT AND TRADEMARK OFFICE
CERTIFICATE OF CORRECTION

| | |
|---|---|
| PATENT NO. | : 11,065,414 B2 |
| APPLICATION NO. | : 16/056176 |
| DATED | : July 20, 2021 |
| INVENTOR(S) | : Peter Nigel Coleman et al. |

It is certified that error appears in the above-identified patent and that said Letters Patent is hereby corrected as shown below:

In the Specification

Column 3, Line 21, delete "passageway" and insert -- passageway. --.

Column 10, Line 50, delete "tube" and insert -- tube. --.

Column 16, Line 8, delete "FIG." and insert -- FIGS. --.

Column 19, Line 4, delete "tube" and insert -- tube, --.

In the Claims

Column 23, Line 36, Claim 1, delete "A medical comprising:" and insert -- A medical tube comprising: --.

Signed and Sealed this
Fifth Day of September, 2023

Katherine Kelly Vidal
*Director of the United States Patent and Trademark Office*